(12) United States Patent
Dumaitre et al.

(10) Patent No.: US 6,867,225 B2
(45) Date of Patent: Mar. 15, 2005

(54) THIAZOLE OR OXAZOLE DERIVATIVES WHICH ARE USEFUL IN THE TREATMENT OF CARDIOVASCULAR AND RELATED DISEASES

(75) Inventors: Bernard Andre Dumaitre, Les Ulis (FR); Romain Luc Gosmini, Les Ulis (FR)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/478,259

(22) PCT Filed: May 29, 2002

(86) PCT No.: PCT/EP02/05885

§ 371 (c)(1),
(2), (4) Date: Apr. 29, 2004

(87) PCT Pub. No.: WO02/096894

PCT Pub. Date: Dec. 5, 2002

(65) Prior Publication Data

US 2004/0176427 A1 Sep. 9, 2004

(30) Foreign Application Priority Data

May 31, 2001 (GB) .............................................. 0113233

(51) Int. Cl.[7] .................... A61K 31/421; A61K 31/426; C07D 263/34; C07D 277/56

(52) U.S. Cl. ....................... 514/365; 514/340; 514/342; 514/374; 546/269.7; 546/271.4; 548/200; 548/201; 548/236

(58) Field of Search .................... 546/269.7, 271.4; 548/200, 201, 236; 514/340, 342, 365, 374

(56) References Cited

U.S. PATENT DOCUMENTS 5,859,051 A  1/1999  Adams et al.
6,518,290 B1 * 2/2003  Sierra .......................... 514/365

FOREIGN PATENT DOCUMENTS

WO  WO 01/40207  6/2001
WO  WO 02/50047  6/2002

* cited by examiner

Primary Examiner—Fiona T. Powers
(74) Attorney, Agent, or Firm—Robert H. Brink

(57) ABSTRACT

A compound of formula (I) and pharmaceutically acceptable salts, solvates and hydrolysable esters thereof (I)

Wherein
$R^1$ and $R^2$ are independently H or $C_{1-3}$ alkyl or $R^1$ and $R^2$ which are bonded to the same carbon atom may together with the carbon atom to which they are bonded form a 3–5 membered cycloalkyl ring;
$X_1$ represents O or S;
Each $R^3$, $R^4$, $R^8$ and $R^9$ independently represents H, halogen, —$CH_3$ and —$OCH_3$;
$R^5$ represents H or $C_{1-6}$ alkyl or $R^4$ and $R^5$ together form a 3–6 membered cycloalkyl ring.

$X_2$ represents NH, NCH$_3$ or O;
One of Y and Z is N, and the other is O or S;
$R^6$ represents phenyl or pyridyl (wherein the N is in position 2 or 3) and is optionally substituted by one or more halogen, $CF_3$, $C_{1-6}$ straight or branched alkyl (optionally substituted by halogen), with the provision that when $R^6$ is pyridyl, the N is unsubstituted.

$R^7$ represents $C_{1-6}$alkyl, (optionally substituted by one or more halogens), —$C_{0-8}$alkyl-5 membered heteroaryl, $C_{0-6}$alkyl-(O)$_n$-phenyl, wherein n is 0 or 1, with the proviso that when $R^1$ and $R^2$ are methyl, $R^8$ and $R^9$ are H, $R^5$ is H, then $R^7$ cannot be $CH_3$ or $CF_3$.

19 Claims, No Drawings

THIAZOLE OR OXAZOLE DERIVATIVES WHICH ARE USEFUL IN THE TREATMENT OF CARDIOVASCULAR AND RELATED DISEASES

This application is filed pursuant to 35 U.S.C. § 371 as a United States National Phase Application of International Application No. PCT/EP02/05885 filed May 29,2002, which claims priority from GB 0113233.1 filed May 31, 2001

The present invention relates to certain novel compounds. In particular, the present invention relates to compounds that activate the alpha subtype of the human peroxisome proliferator activated receptor ("hPPAR alpha"). The present invention also relates to methods for preparing the compounds and methods for prevention or treatment of PPAR alpha mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e., currently there are no drugs on the market that are useful for raising HDL-c >40%). (Bisgaier, C. L.; Pape, M. E. Curr. Pharm. Des. 1998, 4, 53–70).

Syndrome X (including metabolic syndrome) is loosely defined as a collection of abnormalities including hyperinsuinlemia, obesity, elevated levels of trigycerides, uric acid, fibrinogen, small dense LDL-c particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example, Willson, T. M. and Wahli, W., Curr. Opin. Chem. Biol., (1997), Vol. 1, pp 235–241.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, Trends Endocrin. Met 291–296, 4 (1993)).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.).

Fibrates are a class of drugs which may lower serum triglycerides 20–50%, lower LDL-c 10–15%, shift the LDL particle size from the more atherogenic small dense to normal dense LDL-c, and increase HDL-c 10–15%. Experimental evidence indicates that the effects of fibrates on serum lipids are mediated through activation of PPAR alpha. See, for example, B. Staels et al., Curr. Pharm. Des., 1–14, 3 (1), (1997). Activation of PPAR alpha results in transcription of enzymes that increase fatty acid catabolism and decrease de-novo fatty acid synthesis in the liver resulting in decreased triglyceride synthesis and VLDL-c production/secretion. In addition, PPAR alpha activation decreases production of apoC-III. Reduction in apoC-III, an inhibitor of LPL activity, increases clearance of VLDL-c. See, for example, J. Auwerx et al., Atherosclerosis, (Shannon, Irel.), S29-S37, 124 (Suppl), (1996). PPAR alpha ligands may be useful for the treatment of dyslipidemia and cardiovascular disorders, see Fruchart, J. C., Duriez, P., and Staels, B., Curr. Opin. Lipidol. (1999), Vol 10, pp 245–257.

According to a first aspect of the invention there is provided a compound of formula (I) and pharmaceutically acceptable salts, solvates and hydrolysable esters thereof:

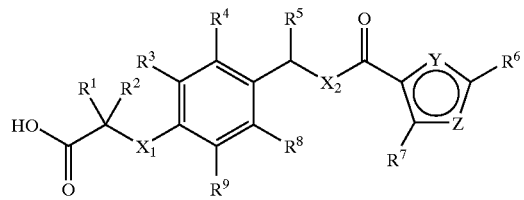

Wherein $R^1$ and $R^2$ are independently H or $C_{1-3}$ alkyl or $R^1$ and $R^2$ which are bonded to the same carbon atom may together with the carbon atom to which they are bonded form a 3–5 membered cycloalkyl ring;

$X_1$ represents O or S;

Each $R^3$, $R^4$, $R^8$ and $R^9$ independently represents H, halogen, —$CH_3$ or —$OCH_3$;

$R^5$ represents H or $C_{1-6}$ alkyl or $R^4$ and $R^5$ together form a 3–6 membered cycloalkyl ring.

$X_2$ represents NH, $NCH_3$ or O;

One of Y and Z is N, and the other is O or S;

$R^6$ represents phenyl or pyridyl (wherein the N is in position 2 or 3) and is optionally substituted by one or more halogen, $CF_3$, $C_{1-6}$ straight or branched alkyl (optionally substituted by halogen), with the provision that when $R^6$ is pyridyl, the N is unsubstituted.

$R^7$ represents $C_{1-6}$alkyl, (optionally substituted by one or more halogens), —$C_{0-6}$alkyl- 5 membered heteroaryl, $C_{0-6}$alkyl —$(O)_n$— phenyl, wherein n is 0 or 1 with the proviso that when $R^1$ and $R^2$ are methyl, $R^8$ and $R^9$ are H, $R^5$ is H, then $R^7$ cannot be $CH_3$ or $CF_3$.

In another aspect, the present invention discloses a method for prevention or treatment of a human PPAR ("hPPAR") mediated diseases or conditions comprising administration of a therapeutically effective amount of a compound of this invention. hPPARmediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lining and gut and regulation of appetite and food intake in subjects suffering from disorders such as obesity, bulimia, and anorexia nervosa. In particular, the compounds of this invention are useful in the treatment and prevention of cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

In another aspect, the present invention provides a method of treatment of a patent suffering from a hPPAR mediated disease or condition comprising the administration of a therapeutically effective amount of a compound of the invention.

As used herein, "a compound of the invention" means a compound of formula (I) or a pharmaceutically acceptable salt, solvate, or hydrolyzable ester thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $X_1$ represents O.
Preferably $R^1$ and $R^2$ are methyl.
Preferably $R^3$ is methyl or H.
Preferably $R^4$ is H or together with $R^5$ forms a 6 membered cycloalkyl ring.
Preferably $R^8$ and $R^9$ both represent H.
Preferably $R^5$ represents $CH_3$, H or together with $R^4$ forms a 6 membered cycloalkyl ring.
Preferably $X_2$ represents NH.
Preferably Z represents N.
Preferably Y represents S.
Preferably $R^7$ represents $CH_3$—$CH_2$—O-phenyl, or $CH_2$—O-thiophene (wherein the S is in position 2).
Preferably $R^6$ is phenyl, optionally substituted. Preferably $R^6$ is mono or disubstituted. Preferably when $R^6$ is pyridyl the N is in the 2 position. $R^6$ preferably is monosubstituted in the para position and is more preferably phenyl. A preferred substituent is $CF_3$.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferably, the compounds of formula (I) are hPPAR agonists. The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPAR delta, in the binding assay described below, and which achieve at least 50% activation of the relevant PPAR relative to the appropriate indicated positive control in the transfection assay described below at concentrations of 10–5 M or less. More preferably, the compounds of this invention achieve 50% activation of at least one human PPAR in the relevant transfection assay at concentrations of 10–6 M or less. More preferably the compounds of the invention achieve 50% activation of at least one human PPAR in the relevant transfection assay at concentrations of 10–7M or less.

Preferably the compounds are hPPAR alpha agonists.

Most preferably, the compounds of formula (I) are selective hPPAR alpha agonists. As used herein, a "selective hPPAR alpha agonist" is a hPPAR alpha agonist whose $EC_{50}$ for PPAR alpha is at least 10 fold lower than its $EC_{50}$ for PPAR gamma and PPAR delta. Such selective compounds may be referred to as "10-fold selective." $EC_{50}$ is defined in the transfection assay described below and is the concentration at which a compound achieves 50% of its maximum activity. Most preferred compounds are greater than 100-fold selective hPPAR alpha agonists.

Preferred compounds of the invention include:
2-methyl-2-[3-methyl-4-{[(4-phenoxymethyl-2-[4-trifluoromethylphenyl]-thiazol-5-ylcarbonyl)amino]methyl}phenoxy]propionic acid ethyl ester
2-methyl-2-[3-methyl-4-{[(4-phenoxymethyl-2-[4-trifluoromethylphenyl]-thiazol-5-ylcarbonyl)amino]methyl}phenoxy]propionic acid
2-methyl-2-[3-methyl-4-{[(4-thiophen-2-ylmethyl-2-[4-trifluoromethylphenyl]-thiazol-5-ylcarbonyl)amino]methyl}phenoxy]propionic acid ethyl ester
2-methyl-2-[3-methyl-4-{[(4-thiophen-2-ylmethyl-2-[4-trifluoromethylphenyl]-thiazol-5-ylcarbonyl)amino]methyl}phenoxy]propionic acid
2-Methyl-2-[5-{[(4-Methyl-2-[4-trifluoromethylphenyl]-thiazol-5-ylcarbonyl)amino]-5,6,7,8-tetrahydronaphtalen-2-yloxy ]propionic acid ethyl ester
2-methyl-2-[3-methyl-4-{1-[(4-methyl-2-[4-trifluoromethylphenyl]-thiazol-5-ylcarbonyl)amino]ethyl}phenoxy]propionic acid ethyl ester More preferred compound of the invention is:
2-Methyl-2-[5-{[(4-Methyl-2-[4-trifluoromethylphenyl]-thiazol-5-ylcarbonyl)amino]-5,6,7,8-tetrahydronaphtalen-2-yloxy ]propionic acid Most preferred compound of the invention is:
2-methyl-2-[3-methyl-4-{1-[(4-methyl-2-[4-trifluoromethylphenyl]-thiazol-5-ylcarbonyl)amino]ethyl}phenoxy]propionic acid The preferred compounds listed above are selective hPPAR alpha agonists.

Those skilled in the art will recognize that stereocenters exist in compounds of formula (I). Accordingly, the present invention includes all possible stereoisomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds. In particular, in many of the preferred compounds of this invention the carbon atom to which $R^1$ and $R^5$ are bonded is chiral. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma agonists (for example thiazolidinediones such as e.g. Pioglitazone and Rosiglitazone). The compounds may also be used in combination with antihypertensive agents such as calcium channel antagonists and ACE inhibitors. The invention thus provides in a further aspect the use of a combination comprising a compound of formula (I) with a further therapeutic agent in the treatment of a hPPAR alpha mediated disease.

When the compounds of formula (I) are used in combination with other therapeutic agents, the compounds may be administered either sequentially, or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by a general process wherein a moiety like (A) is coupled to an acid (B) using a peptide coupling reaction. Note that this synthesis may be carried out with the acid group protected by R. Preferably, R is $C_{1-6}$alkyl which can be hydrolyzed off to give an acid of Formula (I), or if readily hydrolyzable, the resulting ester can be administered.

Compounds of formula (A) and (B) may be commercially available or their synthesis will be apparent to a skilled person, eg by analogous methods to those described below.

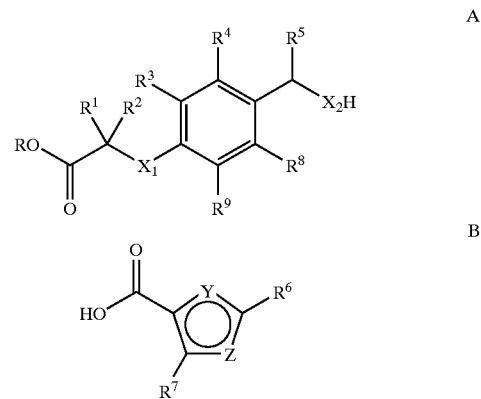

The invention is further illustrated by the following examples which should not be construed as constituting a limitation thereto.

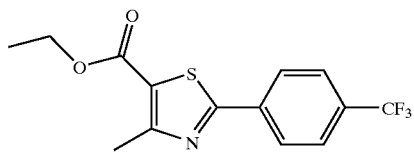

Intermediate 1:

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent was removed in vacuo. The final product (intermediate 1) was recrystallized from a minimum of MeOH to afford 40 g (59%) of final product as a white solid. $^1$H NMR (CDCl$_3$): δ8.10 (d, 2H), 7.70 (d, 2H), 4.40 (q, 2H), 2.80 (s, 3H), 1.4 (t, 3H).

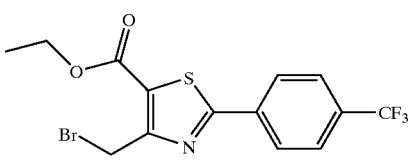

Intermediate 2:

To a solution of intermediate 1 (15.75 g, 50 mmol) in 250 mL of $CCl_4$ is added NBS (1.96 g, 11 mmol). To the resulting suspension is added AIBN (1 g) and the mixture is heated to 80° C. for 3 hours then filtered off and concentrated under vacuo. The residue is taken up in $CH_2Cl_2$ (500 mL) and washed with brine (100 mL). The organic layer is dried over $Na_2SO_4$, filtered and concentrated to dryness to afford after column chromatography eluting with $CH_2Cl_2/C_6H_{12}$ (40/60) the title compound (73%).

GC/MS: m/z: 393–395

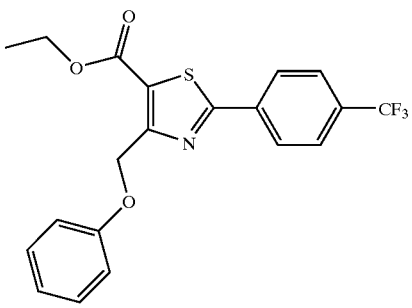

Intermediate 3:

To a solution of Intermediate 2 (394 mg, 1 mmol) in 25 mL of acetone are added Phenol (100 mg, 1.1 mmol) and $Cs_2CO_3$ (355 mg, 1.1 mmol). The resulting mixture is heated at 50° C. for 12 hours. After filtration, concentration under vacuum the residue is taken up with $CH_2Cl_2$ (100 mL) and washed with NaOH 0.1N (10 mL). The organic layer is dried over $Na_2SO_4$, filtered, concentrated to dryness to give the title compound as a white solid (94%). $^1$H NMR ($CDCl_3$): δ8.05 (d, 2H), 7.65 (d, 2H), 7.2 (m, 2H), 7.0 (d, 2H), 6.9 (t, 1H), 5.45 (s, 2H), 4.25 (q, 2H), 1.25 (t, 3H).

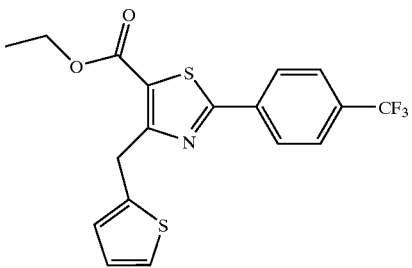

Intermediate 4:

To a solution of Intermediate 2 (1 g, 2.5 mmol) in 50 mL of DME under a nitrogen atmosphere are added (87 mg, 0.075 mmol) of $Pd(PPh_3)_4$. After heating at 50° C. for 20 minutes a solution of 2-thienyl boronic acid (480 mg, 3.75 mmol) in a mixture of EtOHt DME (20 mL/20 mL) is added followed by a solution of 2M $Na_2CO_3$ (5 mL). After stirring at 50° C. for 18 hours, extraction is done (×3) with $CH_2Cl_2$ (150 mL). The combined organic layers are dried over $Na_2SO_4$, filtered and concentrated to dryness. T.l.c. and $^1$H NMR monitoring of this crude mixture indicate that it stll remains starting intermediate 3. Stirring overnight of the crude product in DMF (10 mL) with PS-Triphenylphosphine (1 g, 1–1.5 mmol/g, Argonaut) allows the trapping of the bromide derivative. After filtration and concentration under vacuum the title compound is obtained as a pale yellow oil (33%).

GC/MS: m/z 397.

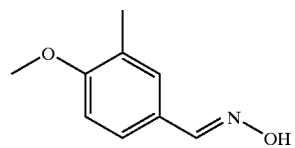

Intermediate 5:

To 4-methoxy-3-methylbenzaldehyde (1 equiv., Acros) in EtOH (150 mL) at rt was added $H_2NOH,HCl$ (1.6 equiv.), (3 equiv.) NaOAc in 150 mL $H_2O$ and the reaction stirred for 2 h. The EtOH was evaporated, and the residue extracted with $CH_2Cl_2$ (3×50 mL). The combined organic layers were washed with $H_2O$, dried over $Na_2SO_4$, filtered and evaporated to dryness to afford the title compound as a white solid (93%).

Mp 71–73° C.

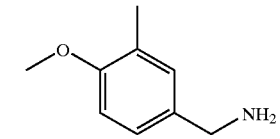

Intermediate 6:

To intermediate 5 (1 equiv.) in MeOH (200 mL) at rt was added $HCO_2NH_4$ (6 equiv.), Pd/C (0.01 equiv.) and molecular sieves. The reaction was then heated to reflux for 18 h. The reaction was filtered through celite, evaporated to dryness and treated with HCl (1N). The aqueous layer was washed with $CH_2Cl_2$, filtered, basified to pH >14 and extracted with $CH_2Cl_2$ (3×50 mL). The combined organic, layers were washed with $H_2O$, dried over $Na_2SO_4$, filtered and evaporated to dryness to afford the title compound as an oil (46%).

MS m/z 151

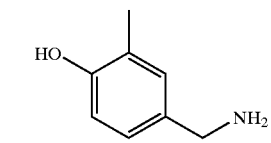

Intermediate 7:

Intermediate 6 (1 equiv.) in excess 40% $HBr/H_2O$ (Aldrich) was refluxed for 18 h. The reaction was then evaporated to dryness to afford the title compound hydrobromide salt as a grey solid (97%).

Mp 235–237° C.

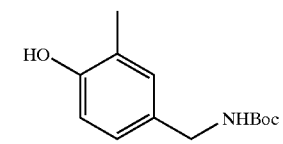

Intermediate 8:

To Intermediate 7 (1 equiv.) in $CH_2Cl_2$ (300 mL) at 0° C. was added $Et_3N$ (3 equiv.). Boc anhydride (0.95 equiv.) in CH$_2$Cl$_2$ (50 mL) was added dropwise. The reaction was allowed to warm to rt and stirring continued for 18 h. HCl (1N) was added and the reaction extracted with CH$_2$Cl$_2$ (3×100 mL). The organic layers washed with H$_2$O, dried over Na$_2$SO$_4$, filtered and the solvent removed under vacuum to afford the title compound as a white solid (96%).
Mp 105–107° C.

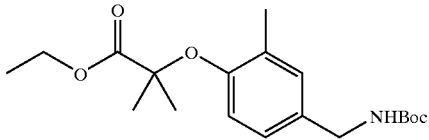

Intermediate 9:

To intermediate 8 (1 equiv.) in DMF (150 mL) was added K$_2$CO$_3$ (3 equiv.) and the reaction heated to 70° C. Ethyl 2-bromo-2-methylproprionate (1.3 equiv.) was added dropwise and the reaction was stirred for 72 h at 70° C. The reaction was poured onto ice and extracted with CH$_2$Cl$_2$ (3×150 mL). The combined organic layers were washed with NaOH (0.5N), then H$_2$O and dried over Na$_2$SO$_4$. The solution was filtered, evaporated to dryness to afford the title compound as an oil (69%). $^1$H NMR (CDCl$_3$): δ7.05 (d, 1H), 6.90 (dd, 1H), 6.60 (d, 1H), 4.80 (bs, 1H), 4.25 (q, 2H), 4.20 (d, 2H), 2.20 (s, 3H), 1.60 (s, 6H), 1.45 (s, 9H), 1.25 (t, 3H).

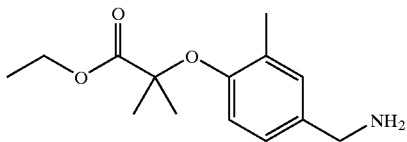

Intermediate 10:

To intermediate 9 (1 equiv.) in CH$_2$Cl$_2$ (10 mL) at rt was added dropwise CF$_3$COOH (7 equiv.) and the reaction stirred at rt for 18 h. The reaction was evaporated to dryness, treated with a sat. K$_2$CO$_3$ solution and extracted with CH$_2$Cl$_2$ (3×150 mL). The combined organic layers were dried over Na$_2$SO$_4$, filtered and evaporated to dryness to afford the title compound as an oil (82%). $^1$H NMR (CDCl$_3$): δ7.00 (d, 1H), 6.90 (dd, 1H), 6.55 (d, 1H), 4.20 (q, 2H), 3.70 (s, 2H), 2.15 (s, 3H), 1.85 (bs, 2H), 1.50 (s, 6H), 1.20 (t, 3H).

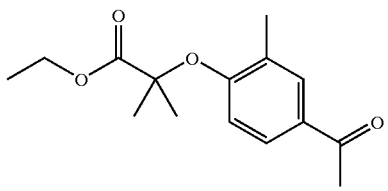

Intermediate 11:

To a solution of 4-hydroxy-3'-methyl-acetophenone (50 g; 0.33 mol) in 1.5 L of acetone is added Cesium carbonate (216.9 g, 0.66 mol). After stirring to reflux for 30 minutes ethyl-2-bromoisobutyrate is added (97 mL, 0.66 mol) to the mixture and the reflux maintained. The same quantities as above of cesium carbonate and ethylbromoisobutyrate are added in two times to complete the reaction. The mixture is then filtered and after concentration to dryness the residue is taken up with 2 L of CH$_2$Cl$_2$ and washed 3 times with water (500 mL). The organic layers are combined and dried over Na$_2$SO$_4$, filtered and concentrated under vacuo to afford the title compound as a brown oil (87%). $^1$H NMR (CDCl$_3$): δ7.71 (s, 1H), 7.61 (d, 1H), 6.5 (d,1H), 4.15 (q, 2H), 2.45 (s, 3H), 2.20 (s, 3H), 1.58 (s, 6H), 1.15 (t, 3H)

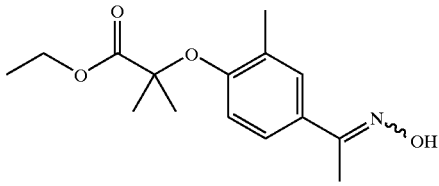

Intermediate 12:

To a solution of Intermediate 11 (7.55 g, 28.6 mmol) is added hydroxylamine hydrochloride (3.2 g, 45.76 mmol) and sodium acetate (7 g, 85.8 mmol) in solution in water (75 mL). After stirring at room temperature for 6 hours EtOH is removed under reduced pressure and the residue taken up with CH$_2$Cl$_2$ (500 mL) and washed with water (100 mL). The organic layer is dried over Na$_2$SO$_4$, filtered and concentrate to dryness to afford the title compound (96%) as an oil.

$^1$H NMR (CDCl$_3$): δ7.30 (s, 1H), 7.2 (d, 1H), 6.55 (d, 1H), 4.15 (q, 2H), 2.15 (s, 6H), 1.55 (s, 6H), 1.15 (t, 3H).

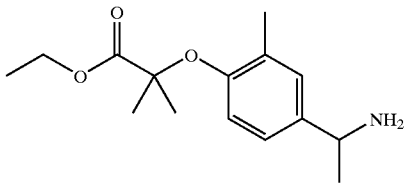

Intermediate 13:

To a solution of intermediate 12 (7.7 g, 27.6 mmol) in MeOH (150 mL) under a nitrogen atmosphere are added ammonium formiate (10.4 g, 166 mmol) and 10% Pd/C (700 mg). The mixture is heated to reflux for 24 hours and filtered on a celite pad. After washing with MeOH (100 mL) the filtrate is concentrated under vacuum and the residue taken up with CH$_2$Cl$_2$ (250 mL) and 1N HCl (250 mL). The aqueous layer is separated and basified to pH=14 with 35% NaOH. Extraction is then carried out with CH$_2$Cl$_2$ (300 mL) and the organic layer is dried over Na$_2$SO$_4$, filtered and concentrated to dryness to afford the expected compound as a colorless oil (57%).

MS: m/z 265

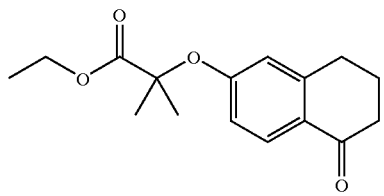

Intermediate 14:

6-hydroxy-1-tetralone (20 g; 0.125 mol) and potassium carbonate (28 g; 0.2 mol) were stirred at room temperature in 250 mL of Methylisopropylketone during 15 minutes. Ethylbromoisobutyrate (20 mL;0.13 mol) was added and the mixture was refluxed 10 hours with stirring. The mixture was filtrated, concentrated, treated with water and extracted with diethyl ether. The ethereal solution was washed with diluted sodium hydroxide, water, dried over Na$_2$SO$_4$ and concentrated under vacuo to give the title compound (42%) as an oil.

MS:m/z 276

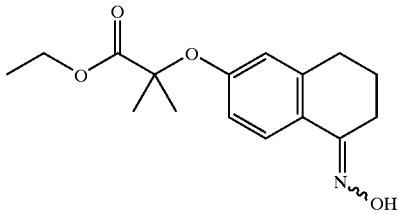

Intermediate 15:

To a solution of Intermediate 14 (2 g; 7.2 mmol) in 50 mL of Ethanol was added a solution of hydroxylamine hydrochloride (1 g; 15 mmol) in water (5 mL), followed by sodium acetate (1.2 g; 15 mmol). The mixture was stirred at reflux during 16 hours. The mixture was then concentrated to dryness and heated with water to give an oil which crystallized upon standing. After filtration, washing with water and drying, the title compound was obtained as cream crystals (81%).

Mp 80° C.
MS: m/z 291

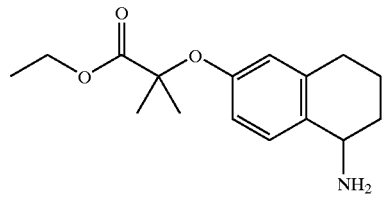

Intermediate 16:

A mixture of Intermediate 15 (1.6 g; 5.5 mmol) in 100 mL of Ethanol and 10% Pd/C (0.2 g) was hydrogenated 16 hours at 50° C. in a Parr apparatus under a pressure of 30 bars. After filtration through a celite pad and concentration under vacuo, the title compound is obtained as an oil (79%). $^1$H NMR (CDCl$_3$): δ7.15 (d, 1H), 6.55 (d, 1H), 6.45 (s, 1H), 4.15 (q, 2H), 3.9 (m, 1H) 2.65 (m, 2H), 2.2 (m, 2H), 1.9 (m, 2H), 1.65 (m,2H), 1.5 (s,6H), 1.2 (t,3H)

General Procedure 1 for the Hydrolysis of the Ethyl Esters

To a solution of the ethyl ester (1 mmol) in MeOH (50 mL) was added (3 equiv.) NaOH (1N) and the mixture heated to 60° C. overnight. The reaction is cooled to room temperature and the solution acidified with HCl (1N) and extracted with CH$_2$Cl$_2$ (3×25 mL). The combined organic layers washed with H$_2$O, dried over Na$_2$SO$_4$, filtered and evaporated to dryness. The solid was titrated with Et$_2$O, collected and dried under vaccum to afford the final product.

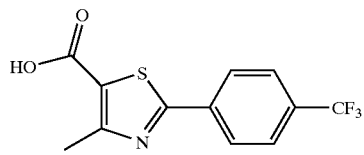

Intermediate 17:

Intermediate 1 was reacted as described in general procedure 1 to afford intermediate 17 (89%) as a white solid. $^1$H NMR (DMSO-d$_6$): δ13.55 (bs, 1H), 8.25 (d, 2H), 7.95 (d, 2H), 2.75 (s, 3H).

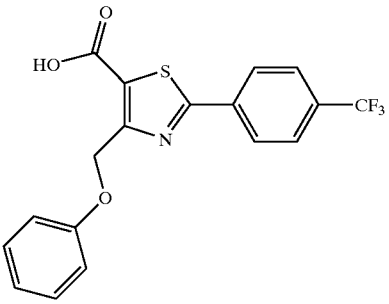

Intermediate 18:

Intermediate 3 was reacted as described in general procedure 1. After removal of EtOH under reduced pressure, the residue was treated with HCl and the solid collected, washed with water and dried under vacuum to afford a white powder (86%). $^1$H NMR (CDCl$_3$): δ8.05 (d, 2H), 7.65 (d, 2H), 7.2 (m, 2H), 6.95 (d, 2H), 6.9 (t, 1H), 5.45 (s, 2H).

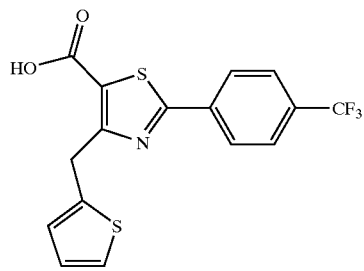

Intermediate 19:

Intermediate 4 (330 mg, 0.85 mmol) was reacted as described in general procedure 1. After removal of EtOH under reduced pressure, the residue was taken up with EtOAc (150 mL), the aqueous phase acidified to pH=1 with HCl 1N. The organic layer is dried over Na$_2$SO$_4$, filtered and concentrated to dryness to afford after column chromatography eluting with CH$_2$Cl$_2$/MeOH (85/15) the title compound (98%) as an off-white solid.

MS (AP+): 369.88 (M+1)

General Procedure 2 for the Peptide Coupling Reaction between Intermediates of Type A and B To intermediate B (1 equiv.) in CH$_2$Cl$_2$ (75 mL) at rt was added HOBT (1.1 equiv.), EDC (1.1 equiv.) and Et$_3$N (3 equiv.). To the mixture was added intermediate A and the reaction was stirred at rt for 18 h. The reaction was washed with HCl (1N), NaOH (1N) and 2×H$_2$O. The organic layer was dried over Na$_2$SO$_4$, filtered and evaporated to dryness. The crude compound was chromatographed or crystallized as necessary to afford the final product.

General Procedure 3 for the Peptide Coupling Reaction between Intermediates of Type A and B To intermediate B (1 equiv.) in DMF (25 mL) at rt was added HATU (1.1 equiv.), intermediate A (1 equiv.) and Et$_3$N (2 equiv.). The reaction was stirred at rt for 18 h. The mixture is evaporated to dryness under vacuum and the residue is taken up in 200 mL of CH2Cl2 and washed with brine (50 mL). The organic layer was dried over Na$_2$SO$_4$, filtered and evaporated to dryness. The crude compound was chromatogaphed or crystallized as necessary to afford the final product.

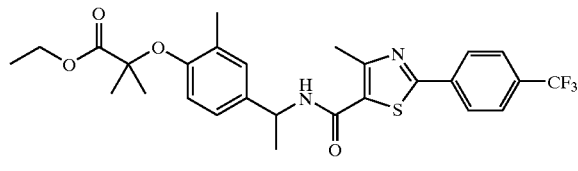

EXAMPLE 1

2-methyl-2-[3-methyl-4-{1-[(4-methyl-2-[4-trifluoromethylphenyl-thiazol-5-ylcarbonyl)amino]ethyl}phenoxy]propionic acid ethyl ester Intermediate 22 and intermediate 5 were reacted as described in general procedure 3 to afford the title compound as a white solid (94%). Chromatographed: $CH_2Cl_2$/EtOAc (93/7)

Mp 116° C.

MS(AP+): 535.35 (M+1)

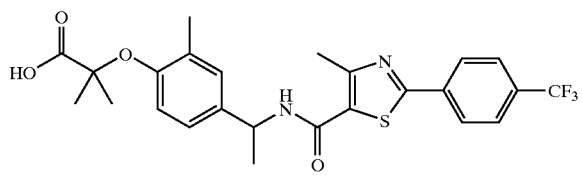

EXAMPLE 2

2-methyl-2-[3-methyl-4-{1-[(4-methyl-2-[4-trifluoromethylphenyl]-thiazol-5-ylcarbonyl)amino]ethyl}phenoxy]propionic acid Example 1 was reacted as described in general procedure 1. After chromatography eluting with $CH_2Cl_2$/MeOH (95:5) the title compound was obtained from a recrystallization in toluene as a white solid (63%). MS(AP−): 505.1 (M−1)

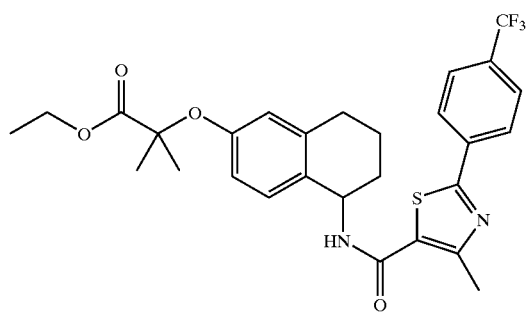

EXAMPLE 3

2-Methyl-2-[5-{[(4-Methyl-2-[4-trifluoromethyl-phenyl]-thiazol-5-ylcarbonyl)amino]-5,6,7,8-tetrahydronaphtalen-2-yloxy]propionic acid ethyl ester Intermediate 19 and Intermediate 2 were reacted as described in general procedure 2 to afford the title compound as a white solid after recrystallization with acetonitrile (74%).

Mp 142° C.

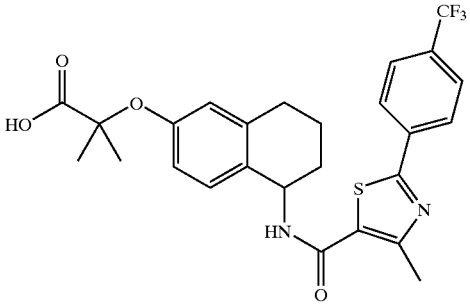

EXAMPLE 4

2-Methyl-2-[5-{[(4-Methyl-2-[4-trifluoromethyl-phenyl]-thiazol-5-ylcarbonyl)amino]-5,6,7,8-tetrahydronaphtalen-2-yloxy]propionic acid Example 3 was reacted as described in general procedure 1. The title compound was obtained as a white powder (67%) from recrystallization in acetonitrile.

Mp 158–160° C.

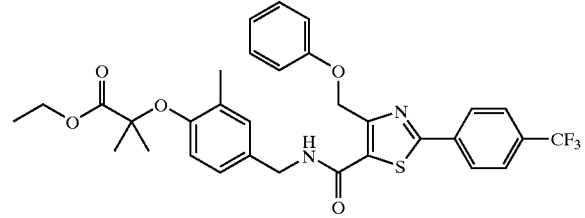

EXAMPLE 5

2-methyl-2-[3-methyl-4-{[(4-phenoxymethyl-2-[4-trifluoromethylphenyl]-thiazol-5-ylcarbonyl)amino]methyl}phenoxy]propionic acid ethyl ester Intermediate 19 and intermediate 5 were reacted as described in general procedure 2 to afford the title compound as a yellow oil (66%). Chromatographed: $C_6H_{12}$/EtOAc (80/20)

MS(AP−): 611.2 (M−1)
MS(AP+): 613.1 (M+1)

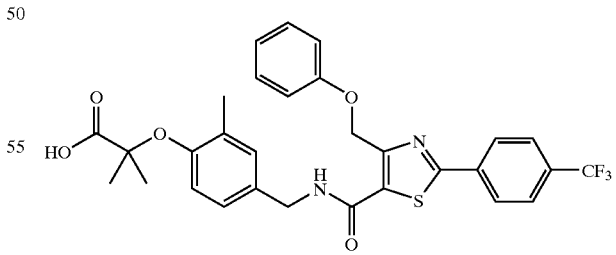

EXAMPLE 6

2-methyl-2-[3-methyl-4-{[(4-phenoxymethyl-2-[4-trifluoromethylphenyl]-thiazol-5-ylcarbonyl)amino]methyl}phenoxy]propionic acid Example 5 was reacted as described in general procedure 1. After chromatography eluting with $CH_2Cl_2$/MeOH (96:4)

the title compound was obtained from recrystallization in hexane as a pale yellow powder (57%).

Mp 146° C.

MS(AP−): 583.1 (M−1)

MS(AP+): 585 (M+1)

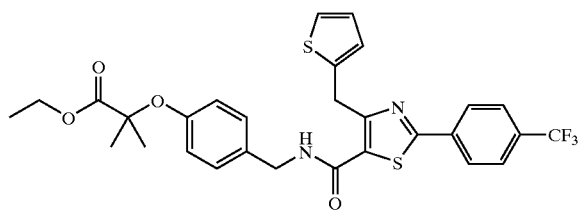

EXAMPLE 7

2-methyl-2-[3-methyl-4-{[(4-thiophen-2-ylmethyl-2-[4-trifluoromethylphenyl]-thiazol-5-ylcarbonyl)amino]methyl}phenoxy]propionic acid ethyl ester Intermediate 7 and intermediate 19 were reacted as described in general procedure 3 to afford the title compound as a colorless gum (49%). Chromatographed: $CH_2Cl_2$/EtOAc (90/10)

MS(AP−): 601.03 (M−1)

MS(AP+): 602.92 (M+1)

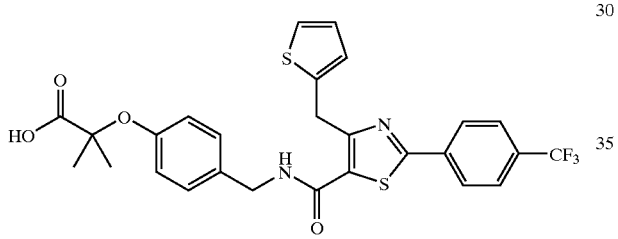

EXAMPLE 8

2-methyl-2-[3-methyl-4-{[(4-thiophen-2-ylmethyl-2-[4-trifluoromethylphenyl]-thiazol-5-ylcarbonyl)amino]methyl}phenoxy]propionic acid Example 7 was reacted as described in general procedure 1. After chromatography eluting with $CH_2Cl_2$/MeOH (95:5) the title compound was obtained from consecutive recrystallizations in hexane and toluene as a white powder (23%).

Mp 147° C.

MS(AP−): 573.1 (M−1)

Binding Assay:

Compounds were tested for their ability to bind to hPPAR gamma hPPAR alpha or PPAR delta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPAR gamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 for PPAR delta (see Brown, P. J et al . *Chem. Biol.* 1997, 4, 909–918 for the structure and synthesis of this ligand and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent K, values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. *Anal. Biochem.* 1998, 257, 112–119).

Transfection Assay:

(i) 2-2-methyl-4-[({4-methyl-2-[4-(trifluoromethyl)phenyl]-1,3-thiazol-5-yl}methyl)sulfanyl]phenoxy}acetic acid.

This compound was used as a PPARdelta reference in the transfection assays described below and was prepared according to the method reported in WO200100603-A1

(ii) 2-methyl-2-[4-{[(4-methyl-2-[4-trifluoromethylphenyl]-thiazol-5-yl carbonyl)amino]methyl}phenoxy] propionic acid.

This compound was used as a PPAR alpha reference in the transfection assay described below and was prepared according to method reported in WO200140207-A1 (and reproduced below).

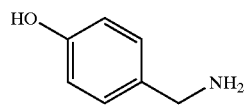

Intermediate (a):

Same procedure as Stout, D. M. *J. Med. Chem.* 1983, 26(6), 808–13. To 4-methoxybenzyl amine (25 g, 0.18 mol; Aldrich) was added 46% HBr in $H_2O$ (106 ml, 0.9 mol; Aldrich). The reaction was refluxed overnight, then the reaction cooled to 0° C. and neutralized to pH7 slowly with $KOH_{(s)}$. The reaction is allowed to stir for ≈30 min, then the solid filtered and dried. The solid redisolved in hot MeOH, filtered and the solution cooled to afford 19 g (85%) intermediate 1. $^1$H NMR (DMSO-$d_6$): δ8.0 (bs, 1H), 7.2 (d, 2H), 6.75 (d, 2H), 3.85 (s, 2H), 3.50 (bs, 2H).

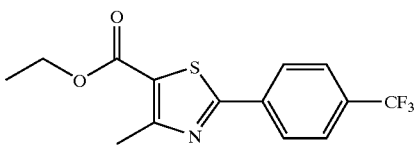

Intermediate (b):

A solution of ethyl 2-chloroacetoacetate (35.3 g, 29.7 mL, 0.21 mol) and 4-(trifluoromethyl)thiobenzamide (44 g, 0.21 mol) in EtOH (300 mL) was refluxed overnight. After cooling to room temperature the solvent removed in vacuo. The final product (intermediate (b)) was recrystallized from a minimum of MeOH to afford 40 g (59%) of final product as a white solid. $^1$H NMR (CDCl$_3$): δ8.10 (d, 2H), 7.70 (d, 2H), 4.40 (q, 2H), 2.80 (s, 3H), 1.4 (t, 3H).

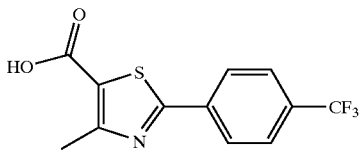

Intermediate (c):

To intermediate (b) (1.84 g, 5.8 mmol) in THF was added 1N LiOH (6 mL, 6 mmol) and the reaction stirred at rt. After ~3 h, the reaction neutralized with 1N HCl, extracted 3×100 mL EtOAc, dried over $Na_2SO_4$, filtered and the solvent removed under vaccum to afford 1.5 g (89%) intermediate (b) as a white solid. $^1$H NMR (DMSO-$d_6$): δ13.55 (bs, 1H), 8.25 (d, 2H), 7.95 (d, 2H), 2.75 (s, 3H).

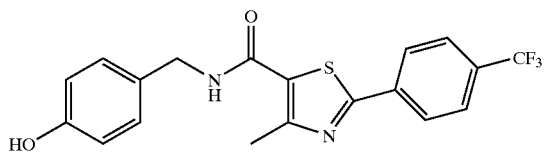

Intermediate (d):

To intermediate (c) (1 g, 7 mmol) in $CH_2Cl_2$/DMF (1:1) was added HOBT (565 mg, 4.2 mmol; Aldrich), EDC (800 mg, 4.2 mmol; Aldrich) and intermediate 1 (860 mg, 7 mmol). The reaction stirred at rt for 18 h. The solvent removed in vacuo, treated with $H_2O$ and extracted 3×100 mL $CH_2Cl_2$. The organic phases combined and washed with 1N HCl, dried over $Na_2SO_4$, filtered and evaporated to afford a mixture (N-substituted and N,O-substituted). The mixture disolved in MeOH and treated with 1N NaOH. The reaction stirred 18 h at 50° C. The solvent removed in vacuo, dissolved in $CH_2Cl_2$, washed with $H_2O$, and dried over $Na_2SO_4$. The solvent evaporated the residue chromatographed ($CH_2Cl_2$/MeOH: 99/1) to afford 610 mg (47%) of intermediate 6 as a white solid. $^1$H NMR (DMSO-$d_6$): δ9.30 (s, 1H), 8.80 (t, 1H), 8.20 (d, 2H), 6.70 (d, 2H), 4.35 (d, 2H), 2.6 (s, 3H).

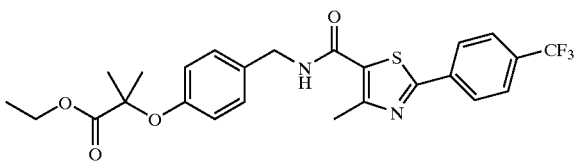

Intermediate (e):

2-methyl-2-[4{[(4-methyl-2-[4-trifluoromethylphenyl]thiazol-5-ylcarbonyl)amino]methyl}phenoxy]propionic acid ethyl ester To intermediate (d) (710 mg, 1.81 mmol) in DMF (50 mL) was added the $K_2CO_3$ (275 mg, 1.99 mmol) followed by the ethyl 2-bromo-2-methylpropanate (280 μL, 1.91 mmol; Aldrich) and the reaction heated to 80° C. After 18 h, the reaction cooled to rt and the solvent removed in vacuo. The residue treated with water (200 mL), extracted 3×50 mL $CH_2Cl_2$, dried over $Na_2SO_4$, filtered and the solvent removed under vaccum. The residue was chromatographed ($CH_2Cl_2$/MeOH: 99/1). To afford 680 mg (77%) of Example 1 as a clear oil. $^1$H NMR(CDCl$_3$): δ7.95 (d, 2H), 7.60 (d, 2H), 7.15 (d, 2H), 6.75 (d, 2H), 6.05 (t, 1H), 4.45 (d, 2H), 4.15 (q, 2H), 2.65 (s, 3H), 1.50 (s, 6H), 1.20 (t, 3H).

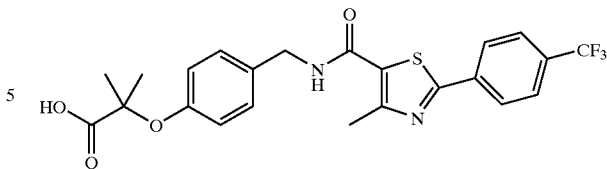

2-methyl-2-[4{[(4-methyl -2-[4-trifluoromethylphenyl]-thiazol-5-ylcarbonyl)amino]methyl}phenoxy]propionic acid To Intermediate (e) (680 mg, 1.39 mmol) in MeOH was added 1N NaOH (1.6 mL, 1.6 mmol) and the reaction stirred at 60° C. After 18 h, the reaction cooled to rt and the solvent evaporated. The residue treated with 1N HCl, extracted 3×20 mL THF and the solvent removed under vacuum. 500 mg (75%) the title compound was precipitated as a white solid from a minimum $CH_2Cl_2$ and pentane. mp: changes the form between 60–70° C.; LC/MS (m/z): 477.22 (100%, AP−), 479.12 (100%, AP+); anal. $C_{23}H_{21}F_3N_2O_4S$: C 5.71 (57.73), H 4.56 (4.42), N 5.77 (5.85), S 6.15 (6.70).

(iii) 5-{4-[2-(Methyl-pyridin-2-yl-amino)-ethoxy]-benzyl}-thiazolidine-2,4-dione This compound was used as a PPAR gamma reference in the transfection assay described below and was prepared according to method reported in *J. Med. Chem.* 1994, 37(23), 3977

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, Oliver T. A.; Wilkison, W. O.; Willson, T. M.; Kliewer, S. A., An antidiabetic thiazolidinedione is a high affinity ligand for peroxisome proliferator-activated receptor gamma (PPAR gamma), *J. Biol. Chem.*, 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPAR gamma assay. The positive control in the hPPAR alpha assays was 2-(2-methyl-3-[3-{3-(4-cyclohexylamino)[6-(4-fluorophenylpiperazin-1-yl)][1,3,5]triazin-2-ylamino}propyl]phenylthio)-2-methylpropionic acid. The positive control for PPAR delta assays was 2-{2-methyl-4-[({4-methyl-2-{-{trifluoromethyl)phenyl]-1,3-thiazol-5-yl}methyl)sulfanyl]phenoxy}acetic acid.

All of the above acid Examples showed at least 50% activation of hPPARa relative to the positive control at concentrations of $10^{-7}$ or less.

Activities in three hPPAR subtypes are reported in the table below for the examples in the acidic form and are expressed in nanomolar.

| Examples | EC50 hPPAR α | EC50 hPPAR δ | EC50 hPPAR γ |
|----------|--------------|--------------|--------------|
| 2 | 1.7 | 190 | 870 |
| 4 | 10 | 8600 | 2224 |
| 6 | 10 | 1130 | 10000 |
| 8 | 17 | 250 | 1710 |

What is claimed is:

1. A compound of formula (I) and pharmaceutically acceptable salts, solvates and hydrolysable esters thereof

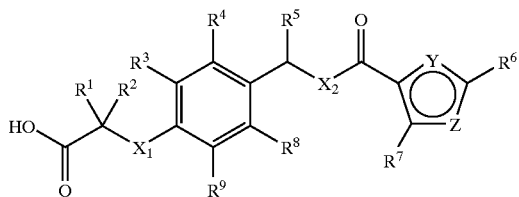

wherein
$R^1$ and $R^2$ are independently H or $C_{1-3}$ alkyl or $R^1$ and $R^2$ which are bonded to the same carbon atom may together with the carbon atom to which they are bonded form a 3–5 membered cycloalkyl ring;
$X_1$ represents O or S;
Each $R^3$, $R^4$, $R^8$ and $R^9$ independently represents H, halogen, —$CH_3$ and —$OCH_3$;
$R^5$ represents H or $C_{1-6}$ alkyl or $R^4$ and $R^5$ together form a 3–6 membered cycloalkyl ring;
$X_2$ represents NH, $NCH_3$ or O;
One of Y and Z is N, and the other is O or S;
$R^6$ represents phenyl or pyridyl (wherein the N is in position 2 or 3) and is optionally substituted by one or more halogen, $CF_3$, $C_{1-6}$ straight or branched alkyl (optionally substituted by halogen), with the provision that when $R^6$ is pyridyl, the N is unsubstituted;
$R^7$ represents $C_{1-6}$alkyl, (optionally substituted by one or more halogens), —$C_{0-6}$alkyl-5 membered heteroaryl, $C_{0-6}$alkyl-(O)$_n$-phenyl, wherein n is 0 or 1, with the proviso that when $R^1$ and $R^2$ are methyl, $R^8$ and $R^9$ are H, $R^5$ Is H, then $R^7$ cannot be $CH_3$ or $CF_3$.

2. A compound according to claim 1 which is a selective hPPAR alpha agonist.

3. A compound according to claim 1 wherein $X_1$ represents O.

4. A compound according to claim 1 wherein $R^1$ and $R^2$ are methyl.

5. A compound according to claim 1 wherein $R^3$ is methyl or H.

6. A compound according to claim 1 wherein $R^4$ is H or together with $R^5$ forms a 6 membered cycloalkyl ring.

7. A compound according to claim 6 wherein $R^8$ and $R^9$ are H.

8. A compound according to claim 1 wherein $R^5$ represents $CH_3$ or together with $R^4$ forms a 6 membered cycloalkyl ring.

9. A compound according to claim 1 wherein $X_2$ represents NH.

10. A compound according to claim 1 wherein Z represents N.

11. A compound according to claim 1 wherein Y represents S.

12. A compound according to claim 1 wherein $R^6$ is monosubstituted.

13. A compound according to claim 12 wherein $R^6$ is monosubstituted in the para position.

14. A compound according to claim 1 wherein $R^6$ is phenyl.

15. A compound according to claim 1 selected from the group consisting of:
2-methyl-2-[3-methyl-4-{[(4-phenoxymethyl-2-[4-trifluoromethylphenyl]-thiazol -5-ylcarbonyl)amino]methyl}phenoxy]propionic acid ethyl ester,
2-methyl-2-[3-methyl-4-{[(4-phenoxymethyl-2-[4-trifluoromethylphenyl]-thiazol -5-ylcarbonyl)amino]methyl}phenoxy]propionic acid,
2-methyl-2-[3-methyl-4-{[(4-thiophen-2-ylmethyl-2-[4-trifluoromethylphenyl]-thiazol-5-ylcarbonyl)amino]methyl}phenoxy]propionic acid ethyl ester,
2-methyl-2-[3-methyl-4-{[(4-thiophen-2-ylmethyl-2-[4-trifluoromethylphenyl]-thiazol-5-ylcarbonyl)amino]methyl}phenoxy]propionic acid,
2-Methyl-2-[5-{[(4-Methyl-2-[4-trifluoromethyl-phenyl]-thiazol-5-ylcarbonyl)amino]-5,6,7,8-tetrahydronaphtalen-2-yloxy]propionic acid ethyl ester,
2-methyl-2-[3-methyl-4-{1-[(4-methyl-2-[4-trifluoromethylphenyl]-thiazol -5-ylcarbonyl)amino]ethyl}phenoxy]propionic acid ethyl ester,
2-Methyl-2-[5-{[(4-Methyl-2-[4-trifluoromethyl-phenyl]-thiazol-5-ylcarbony)amino]-5,6,7,8-tetrahydronaphtalen-2-yloxy]propionic acid,
2-methyl-2-[3-methyl-4-{1-[(4-methyl-2-[4-trifluoromethylphenyl]-thiazol -5-ylcarbonyl)amino]ethyl}phenoxy]propionic acid, and pharmaceutically acceptable salts, solvates and hydrolysable esters thereof.

16. A compound selected from the group consisting of 2-methyl-2-[3-methyl-4-{1-[(4-methyl-2-[4-trifluoromethylphenyl]-thiazol-5-ylcarbonyl)amino]ethyl}phenoxy]propionic acid, and pharmaceutically acceptable salts, solvates and hydrolysable esters thereof.

17. A pharmaceutical composition comprising a compound according to claim 1.

18. A pharmaceutical composition according to claim 17 further comprising a pharmaceutically acceptable diluent or carrier.

19. A method of treating a hPPAR alpha mediated disease or condition in a patient wherein the hPPAR alpha mediated disease or condition is selected from the group consisting of dyslipidemia, syndrome X, heart failure, hypercholesteremia, cardiovascular disease, type II diabetes mellitus, type I diabetes, insulin resistance, hyperlipidemia, obesity, anorexia bulimia and anorexia nervosa comprising the administration of a therapeutically effective amount of a compound according to claim 1.

* * * * *